US00PP28752P2

(12) United States Plant Patent
Hansen

(10) Patent No.: US PP28,752 P2
(45) Date of Patent: Dec. 5, 2017

(54) ***MONARDA* PLANT NAMED 'ROCKIN' RASPBERRY'**

(50) Latin Name: ***Monarda* hybrid**
Varietal Denomination: Rockin' Raspberry

(71) Applicant: Hans A. Hansen, Zeeland, MI (US)

(72) Inventor: Hans A. Hansen, Zeeland, MI (US)

( * ) Notice: Subject to any disclaimer, the term of this patent is extended or adjusted under 35 U.S.C. 154(b) by 0 days.

(21) Appl. No.: 14/999,734

(22) Filed: Jun. 21, 2016

(51) Int. Cl.
*A01H 5/02* (2006.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct cultivar of ornamental cultivar of bee balm plant named *Monarda* 'Rockin Raspberry' has compact, tight clumping habit, with heavily branching stems with upper secondary peduncles extending above the initial flower level and partially obscuring first set of flowers. The dark green leaves are lemony fragrant, have strong resistance to powdery mildew and are heavily tinted with greyed purple while young. Numerous, large, deep raspberry purple-colored flowers are in bloom for a long period beginning cerise-colored flowers creating excellent flower coverage.

1 Drawing Sheet

Botanical classification: *Monarda* hybrid.
Variety denomination: 'Rockin' Raspberry'.

BACKGROUND OF THE INVENTION

The present invention relates to the new and distinct cultivar of bee balm plant, botanically known as *Monarda* 'Rockin' Raspberry', and hereinafter also referred to solely as the cultivar 'Rockin' Raspberry' or the "new plant". The new plant was selected from seed collected by the hybridizer from a formal hybridizing program on Aug. 9, 2012 from designated hybridizing plot of a wholesale perennial nursery in Zeeland, Mich., USA, from an unreleased proprietary hybrid identified as H10-26-07 that was allowed to be insect pollinated on an isolation block on Jun. 12, 2012, and the seeds were harvested on Aug. 9, 2012. The new plant was a single seedling selection originally made in the summer of 2013 from the all the seeds that were sown in the fall of 2012 from this specific process. Further selection was completed in the trial fields of a nursery in Zeeland, Mich. in the summer of 2014 and the plant was assigned the breeder code of H12-62-4.

The new plant has been asexually propagated by shoot tip cuttings originally in 2014 in greenhouses at the same nursery in Zeeland, Mich., and the subsequent asexually propagated plants found to be stable, true to type and identical to the original selection.

No plants of *Monarda* 'Rockin' Raspberry' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventors.

BRIEF SUMMARY OF THE PLANT

*Monarda* 'Rockin' Raspberry' is unique from its parents and all other bee balm plants known to the inventors. It is a complex hybrid probably containing at least the species *M. didyma, M. bartlettii* and *M. fistulosa*. The nearest comparison varieties known to the applicant are: 'Pete's Purple' (not patented), 'Grape Gumball' U.S. Plant Pat. No. 27,498 and 'Leading Lady Plum' U.S. Plant Pat. No. 26,447. The new plant is significantly shorter than 'Pete's Purple', and the flowers are a deep raspberry purple on the new plant. 'Rockin' Raspberry' is slightly taller than 'Leading Lady Plum' and has flower petal color more reddish hue than either and also has a more burgundy tinted young foliage than the comparison plant. 'Leading Lady Plum' has darker spotting on the inside flower petals, however 'Rockin' Raspberry', 'Grape Gumball', 'Pete's Purple' and 'Rockin' Raspberry' do not have spotting on the flower petals. The new plant is also more winter-hardy than 'Pete's Purple'. 'Grape Gumball' is slightly taller and broader in habit with flowers lighter than the new plant, and the flower petals of the new plant are a deeper purple.

The following are traits of *Monarda* 'Rockin' Raspberry' that in combination distinguish it from all other bee balm known to the inventor:

1. Compact, winter-hardy, tight clumping habit.
2. Dark-green leaves with heavy tinting of greyed purple on young expanding foliage.
3. Strong powdery mildew resistant foliage.
4. Large-sized, deep raspberry purple-colored flowers for a long period in summer with excellent flower coverage.
5. Second flush of flower heads held above and partially obscuring initial set.

BRIEF DESCRIPTION OF THE DRAWINGS

The photographs of the new plant demonstrate the unique traits of 'Rockin' Raspberry' and the overall appearance of the two-years-old plant in the full sun trial garden of a wholesale perennial nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
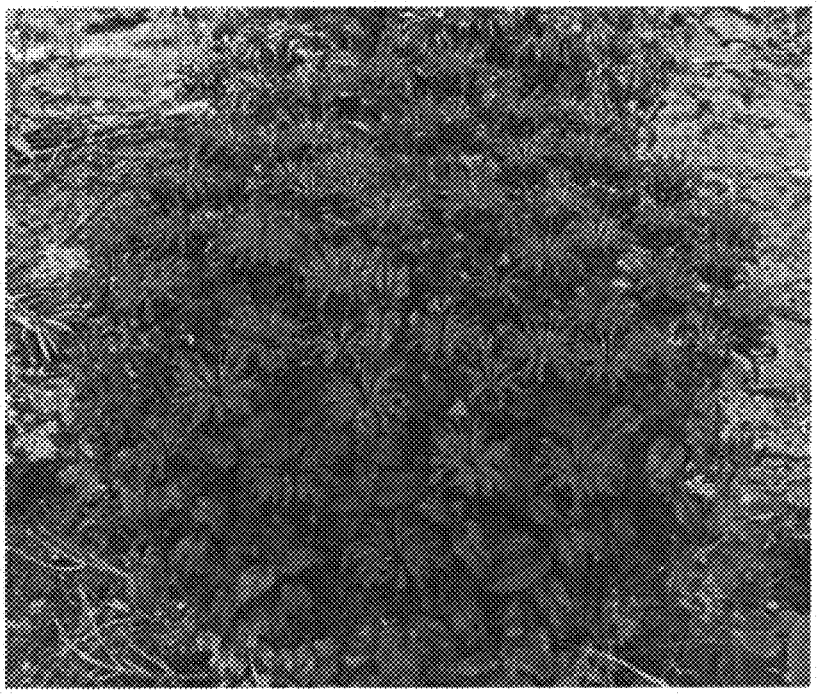
FIG. 1 shows the new plant in flower in the landscape.
Figure 2:
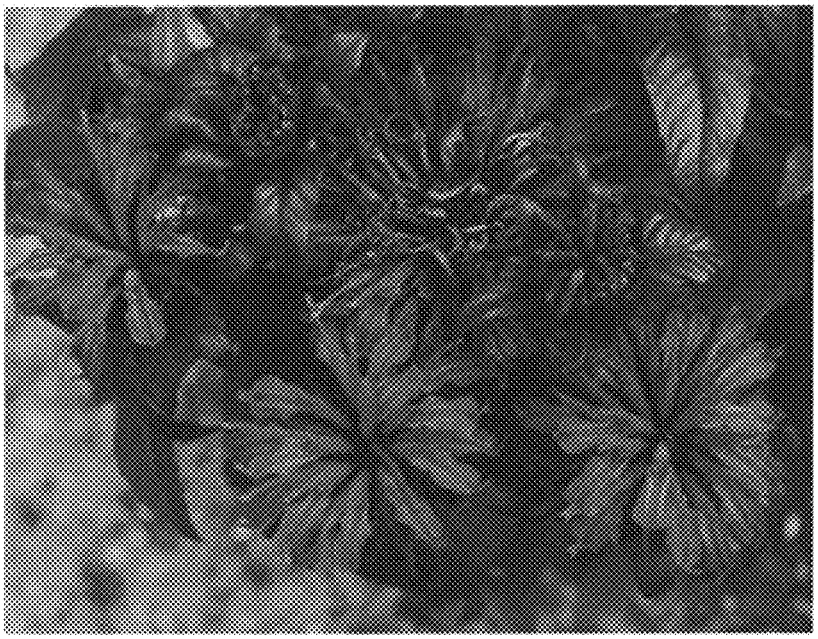
FIG. 2 shows a close-up of the flowers.

The following descriptions and color references are based on the 2001 edition of The Royal Horticultural Society Colour Chart except where common dictionary terms are used. *Monarda* 'Rockin' Raspberry' has not been observed under all possible environments. The phenotype may vary slightly with different growing environments such as temperature, light, fertility, soil pH, moisture and maturity levels, but without any change in the genotype. The following observations and size descriptions are based on two-year old greenhouse-grown plants in gallon containers at a nursery in Zeeland, Mich. with supplemental fertilizer and water as needed but without plant growth regulators or pinching.

Botanical classification: *Monarda* hybrid.

Parentage: Female (seed) parent is the proprietary unreleased *Monarda* hybrid H10-26-07; male (pollen) parent is unknown.

Plant habit: Winter-hardy herbaceous perennial, dense, producing several stems spreading by short rhizomes; about 52.0 cm tall at flowering and about 45.0 cm wide; flowering begins early-summer in Michigan and continuing for about 5 to 8 weeks.

Propagation: Stem cuttings.

Time to produce finished crop in 3.8 liter pots: About 10 to 12 weeks; moderate rate of growth.

Root: Fine, fibrous and freely branching; color creamy white to tan depending on soil type.

Leaves: Simple, lanceolate, opposite, serrated, puberulent above and below; lustrous above, matte below; acute apex, rounded to cordate base; to about 8.4 cm long and 3.8 cm wide, average about 6.5 cm long and 2.8 cm wide.

Leaf color: Young leaves nearest RHS 187A on adaxial surface and on abaxial surface nearest RHS 138A with blushing nearest RHS 187A; leaf base of still expanding leaves nearest RHS N144D on both abaxial and adaxial, distal half of adaxial nearest RHS 187A and abaxial distal half of abaxial nearest RHS 138A with blushing nearest RHS 187A; mature adaxial leaves nearest RHS 137A and abaxial leaves between RHS 137B and RHS 137C.

Foliage fragrance: Pleasant lemony, herbal.

Veins: Pinnate; sparsely puberulent abaxial and adaxial, slightly impressed abaxial and raised adaxial.

Vein color: Mature leaves adaxial midrib nearest RHS N186D proximally with lateral veins and distal midrib nearest RHS 145C; mature abaxial midrib and lateral veins nearest RHS 147C; emerging leaves adaxial midrib and proximal lateral veins nearest RHS 186A, distal lateral veins nearest RHS 144B; emerging leaves abaxial midrib and primary veins between RHS 147C.

Bracts: Between distal leaves and flowers; sessile; margin entire; sparsely puberulent adaxial, puberulent abaxial; seven in larger set; 60 to 70 in smaller set; largest deltoid with acute apex and truncate to attenuate base; smaller set linear with narrowly acute apex and attenuate base. to 7.0 cm long and 4.0 cm wide; decreasing to about 3.0 mm long and less than 0.5 mm across.

Bract color at time of flowering: Larger set abaxial nearest RHS 137A, adaxial nearest RHS 139A; smaller set adaxial some nearest RHS N186B and others nearest RHS 137B with tinting of nearest RHS N186B, abaxial nearest RHS 137C with slight tinting of nearest RHS N186B; adaxial veins nearest RHS N186C in middle and nearest RHS 145C distally and at base; abaxial veins nearest RHS 147D.

Petiole: Pubescent, slightly concavo-convex; to about 6.0 mm long and 3.0 mm across, average about 3.5 mm long and 2.0 mm across.

Petiole color: Adaxial nearest RHS N186C with abaxial between RHS 138B and RHS 138C.

Stems: About 50 per plant; quadrangular, pubescent, about 4.0 mm across at base and about 45 cm long; branching in upper nodes and producing flower heads about 2.0 to 5.0 cm above initial flower heads.

Stem color: Base nearest RHS 187A; distally nearest RHS 144A with a tinting of nearest RHS N186C.

Nodes: About 10 per stem; internode average about 3.5 cm; color distally same as surrounding stem, color proximally developing more intense tinting of nearest RHS N186A.

Flowers: Single, labiate, actinomorphic flowers arranged in terminal verticillate head about 8.5 cm across and 4.5 cm tall opening from the center and progressing outwardly and down; each flower persisting about 5 days in Michigan; numerous, about 280 flowers per head; flower altitude upright to slightly arcuate in center of verticil to horizontal toward outer perimeter of verticil; self-cleaning.

Flower period: Usually late June into August; about six to seven weeks.

Flower fragrance: Lightly sweet.

Buds one to two days prior to opening: Narrowly oblanceolate; tubular; abaxial pubescent; rounded apex; arcuate slightly downward in distal half; about 2.7 cm long, about 3.0 mm tall and about 2.0 mm across in the middle.

Bud color one to two days prior to opening: Nearest RHS 83A in distal one-quarter white, lighter than RHS N155D or RHS 155D.

Petals: Labiate, arcuate downward; basal 2.0 cm fused, split in two in about the distal 1.4 cm forming upper lip and lower lip; upper lip conduplicate into hood about 3.4 cm long and 2.5 mm diameter; lower lip about 3.5 cm long and about 7.0 mm across at widest portion, comprising three terminally divided lobes including two side lobes about 1.0 mm long with rounded apex and center lobe to about 5.0 mm long with emarginate apex indented to about 1.0 mm; both lips glandular to pubescent abaxial with fine hairs the same color as petals; both lips glabrous on adaxial surfaces.

Petal color: Upper lip abaxial distally blend between RHS 83A and RHS N79B, adaxial distally nearest RHS N79B; lower lip nearest RHS N79C abaxial and adaxial distal one-third; middle one-third of upper and lower lips abaxial nearest RHS 77A, adaxial one-third nearest RHS 77B; basal one-third white, lighter than RHS 155D.

Androecium: Two.

*Filaments*.—Two; glabrous; arcuate; basally fused to lower lip; about 1.5 cm long by 0.5 mm diameter; color nearest RHS 72B.

*Anther*.—One; oblong elliptic, dorsifixed, longitudinal; 2.2 mm by 1.0 mm; supported by two terminally fused filaments; color nearest RHS N79B along longitudinal dehiscent line ventrally nearest RHS 72B.

*Pollen*.—Abundant, elliptic to globose, less than 0.1 mm; color nearest RHS 10A.

Gynoecium: One per flower.

*Style*.—Glabrous; arcuate; about 3.5 cm long by about 0.25 mm diameter; color between RHS 77A and RHS 83A toward distal end, lightening to white, lighter than RHS 155D in basal 2.0 cm.

*Stigma*.—Split in two in the distal 2.0 mm, 0.25 mm in diameter; color nearest RHS 83A.

*Ovary*.—Four seeded; about 0.3 mm across by about 0.2 mm tall; color nearest RHS 196B with tip tinted nearest RHS N187B.

*Seeds*.—Up to four per flower; single nutlet; slightly applanate ellipsoid; about 1.5 mm long, 1.0 mm across and about 0.8 mm thick; color blend between RHS 199C and RHS 164B.

Calyx: Five fused sepals, apiculate apex, base fused forming corolla about 11.0 mm long, fused tube about 2.0 mm diameter, apex about 4.5 wide; with apical 2.0 mm separated; adaxial apex glandular, fused adaxial tube glabrous, abaxial puberulent.

Sepal color: Abaxial base nearest RHS 138D, mid-section nearest RHS 139D, apex nearest N187A and veins nearest RHS 147A with tinting of nearest RHS N187A; adaxial base nearest RHS 145D, mid-section nearest RHS 148C, with veins of nearest RHS 138A with tinting of nearest RHS N187A; apex nearest RHS N187A.

Peduncle: Pubescent, stiff, strong, erect, quadrangular to about 0.4 cm across and average about 35.0 cm long; about 70 per plant; naturally branched at nodes.

Peduncle color: Nearest RHS 144A distally with tinting of nearest RHS 187B in regions exposed to high light intensity, and nearest RHS 187B in basal 2.5 cm.

Pedicel: Terete; about 1.0 mm long and 0.7 mm diameter.

Pedicel color: Nearest RHS 148A.

Hardiness: The new plant grows best with plenty of moisture and adequate drainage; hardy to at least from USDA zone 4 through 9.

Disease and pest resistance: Demonstrated strong powdery mildew resistance. Other resistance beyond that of typical bee balm has not been noted.

I claim:

1. A new and distinct cultivar of ornamental bee balm plant, *Monarda* 'Rockin' Raspberry', as herein described and illustrated.

* * * * *